United States Patent
Hou et al.

(10) Patent No.: US 10,519,212 B2
(45) Date of Patent: *Dec. 31, 2019

(54) LONG-ACTING RECOMBINANT FOLLICLE-STIMULATING HORMONE AND USE THEREOF

(71) Applicant: GUANGZHOU VBIO PHARMA CO., LTD., Guangdong (CN)

(72) Inventors: Yongmin Hou, Guangzhou (CN); Yao Lei, Guangzhou (CN); Henglu Deng, Guangzhou (CN)

(73) Assignee: GUANGZHOU VBIO PHARMA CO., LTD., Guangdong (CN)

( * ) Notice: Subject to any disclaimer, the term of this patent is extended or adjusted under 35 U.S.C. 154(b) by 166 days.

This patent is subject to a terminal disclaimer.

(21) Appl. No.: 15/745,207

(22) PCT Filed: Aug. 22, 2014

(86) PCT No.: PCT/CN2014/085012
§ 371 (c)(1),
(2) Date: Jan. 16, 2018

(87) PCT Pub. No.: WO2015/062350
PCT Pub. Date: May 7, 2015

(65) Prior Publication Data
US 2018/0362610 A1    Dec. 20, 2018

(30) Foreign Application Priority Data
Nov. 1, 2013 (CN) .......................... 2013 1 0529898

(51) Int. Cl.
| | | |
|---|---|---|
| *C07K 14/59* | (2006.01) | |
| *C12N 15/79* | (2006.01) | |
| *A61K 38/00* | (2006.01) | |
| *A61P 5/06* | (2006.01) | |

(52) U.S. Cl.
CPC .............. *C07K 14/59* (2013.01); *C12N 15/79* (2013.01); *A61K 38/00* (2013.01); *A61P 5/06* (2018.01); *C07K 2319/00* (2013.01); *C07K 2319/30* (2013.01); *C07K 2319/75* (2013.01); *C12N 2800/60* (2013.01)

(58) Field of Classification Search
None
See application file for complete search history.

(56) References Cited

U.S. PATENT DOCUMENTS

| 7,081,446 | B2 * | 7/2006 | Lustbader | .............. C07K 14/59 514/21.4 |
|---|---|---|---|---|
| 2005/0186662 | A1 * | 8/2005 | Low | ....................... C07K 14/59 435/69.4 |
| 2010/0158911 | A1 * | 6/2010 | Williams | ............... C07K 14/71 424/134.1 |

FOREIGN PATENT DOCUMENTS

| CN | 1131952 A | 9/1996 |
|---|---|---|
| CN | 103539860 A | 1/2014 |
| CN | 103539862 A | 1/2014 |
| WO | 2003/064677 | 8/2003 |
| WO | 2005058953 A2 | 6/2005 |

OTHER PUBLICATIONS

Human Reproduction vol. 20, No. 7 pp. 1805-1813, 2005, Advance Access Publication Apr. 7, 2005, S.C. Low, "Oral and Pulmonary Delivery of FSH—Fc Fusion Proteins via Neonatal Fc Receptor-Mediated Transcytosis".

* cited by examiner

*Primary Examiner* — John D Ulm
(74) *Attorney, Agent, or Firm* — The Dobrusin Law Firm, P.C.

(57) ABSTRACT

Disclosed in the present invention is a long-acting recombinant human follicle-stimulating hormone-Fc fusion protein (referred to as hFSH-Fc for short) and a preparation method thereof, wherein the hFSH-Fc protein is a dimerized fusion protein and the amino acid sequence thereof successively comprises an hFSHβ subunit, CTP, an hFSHα subunit, a flexible peptide linker and human IgG2 Fc variant from N-terminal to C-terminal. Also disclosed in the present invention is the use of the recombinant hFSH-Fc fusion protein composition in preparing drugs in the animal breeding field.

1 Claim, 4 Drawing Sheets
Specification includes a Sequence Listing.

| Human IgG2 Isotype | Amino acid position | | | | | | |
|---|---|---|---|---|---|---|---|
| | 228 | 234 | 235 | 236 | 237 | 330 | 331 |
| IgG2 | Pro | Val | Ala | ……… | | Gly……Ala | Pro |
| IgG2 variant | Pro | Val | Ala | ……… | | Gly……Ala | *Ser* |
FIG. 1
a
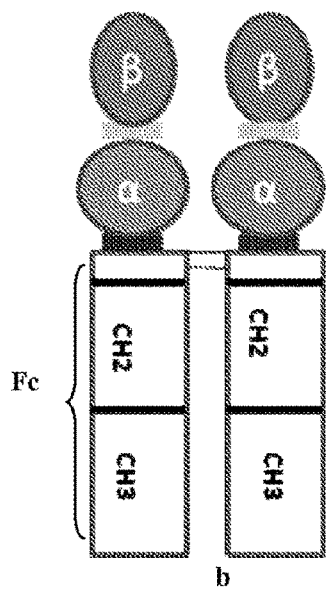
b
FIG. 2

SEQUENCE ID NO: 2

```
   1 M  K  T  L  Q  F  F  F  L  F  C  C  W  K  A  I  C  C  N  S
   1 ATGAAGACCCTGCAGTTCTTTTTCCTGTTTTGCTGTTGGAAGGCAATCTGCTGTAACTCA
  21 C  E  L  T  N  I  T  I  A  I  E  K  E  E  C  R  F  C  I  S
  61 TGTGAGCTGACTAATATCACCATTGCCATCGAAAAAGAGGAATGCAGGTTCTGTATTAGT
  41 I  N  T  T  W  C  A  G  Y  C  Y  T  R  D  L  V  Y  K  D  P
 121 ATCAACACTACCTGGTGCGCTGGCTACTGTTATACAAGGGATCTGGTGTATAAGGACCCA
  61 A  R  P  K  I  Q  K  T  C  T  F  K  E  L  V  Y  E  T  V  R
 181 GCACGGCCCAAAATCCAGAAGACATGCACTTTCAAAGAACTGGTGTACGAGACTGTGAGG
  81 V  P  G  C  A  H  H  A  D  S  L  Y  T  Y  P  V  A  T  Q  C
 241 GTCCCTGGCTGTGCCCACCATGCTGATTCCCTGTACACTTATCCAGTGGCCACCCAGTGC
 101 H  C  G  K  C  D  S  D  S  T  D  C  T  V  R  G  L  G  P  S
 301 CACTGTGGAAAGTGCGATAGTGACTCAACAGACTGTACTGTGCGAGGCCTGGGACCTTCT
 121 Y  C  S  F  G  E  M  K  E  P  R  F  Q  D  S  S  S  S  K  A
 361 TACTGCAGTTTTGGCGAAATGAAGGAGCCCCGTTTCCAGGATTCCAGCTCTAGTAAAGCT
 141 P  P  P  S  L  P  S  P  S  R  L  P  G  P  S  D  T  P  I  L
 421 CCCCCTCCTTCCCTGCCCTCACCCTCAAGACTGCCTGGACCTTCCGACACTCCGATCCTG
 161 P  Q  A  P  D  V  Q  D  C  P  E  C  T  L  Q  E  N  P  F  F
 481 CCACAGGCCCCCGATGTGCAGGACTGCCCTGAATGTACTCTGCAGGAGAACCCCTTCTTT
 181 S  Q  P  G  A  P  I  L  Q  C  M  G  C  C  F  S  R  A  Y  P
 541 TCTCAGCCCGGCGCTCCTATCCTGCAGTGTATGGGATGCTGTTTTAGTAGAGCATATCCT
 201 T  P  L  R  S  K  K  T  M  L  V  Q  K  N  V  T  S  E  S  T
 601 ACCCCACTGCGCTCAAAGAAAACAATGCTGGTCCAGAAGAATGTGACAAGCGAATCTACT
 221 C  C  V  A  K  S  Y  N  R  V  T  V  M  G  G  F  K  V  E  N
 661 TGCTGTGTGGCTAAATCCTACAACCGCGTGACCGTGATGGGCGGCTTCAAGGTGGAGAAT
 241 H  T  A  C  H  C  S  T  C  Y  Y  H  K  S  G  S  G  G  G  S
 721 CACACAGCATGCCATTGTTCTACTTGCTACTACCATAAGAGTGGATCCGGTGGCGGTTCC
 261 G  G  G  S  G  G  G  G  S  V  E  C  P  S  C  P  A  P  P
 781 GGTGGAGGCGGAAGCGGCGGTGGAGGATCAGTGGAGTGCCCTCCATGTCCAGCACCCCCT
 281 V  A  G  P  S  V  F  L  F  P  P  K  P  K  D  T  L  M  I  S
 841 GTCGCAGGTCCATCTGTGTTCCTGTTTCCACCCAAGCCTAAAGACACTCTGATGATCTCC
 301 R  T  P  E  V  T  C  V  V  V  D  V  S  H  E  D  P  E  V  Q
 901 CGCACCCCAGAAGTCACCTGTGTGGTCGTGGATGTGAGCCATGAAGACCCCGAGGTCCAG
 321 F  N  W  Y  V  D  G  V  E  V  H  N  A  K  T  K  P  R  E  E
 961 TTCAATTGGTACGTGGATGGCGTCGAGGTGCACAACGCTAAGACAAAACCTAGAGAAGAG
 341 Q  F  N  S  T  F  R  V  V  S  V  L  T  V  V  H  Q  D  W  L
1021 CAGTTCAACTCTACCTTTCGCGTCGTGAGTGTGCTGACAGTCGTGCACCAGGACTGGCTG
 361 N  G  K  E  Y  K  C  K  V  S  N  K  G  L  P  A  S  I  E  K
1081 AATGGCAAGGAGTATAAGTGCAAAGTGAGCAACAAAGGACTGCCTGCCTCAATCGAAAAG
 381 T  I  S  K  T  K  G  Q  P  R  E  P  Q  V  Y  T  L  P  P  S
1141 ACTATTTCCAAGACCAAAGGACAGCCAAGAGAGCCCCAGGTGTACACCCTGCCTCCAAGC
 401 R  E  E  M  T  K  N  Q  V  S  L  T  C  L  V  K  G  F  Y  P
1201 CGCGAAGAGATGACTAAAAATCAGGTCTCTCTGACCTGTCTGGTGAAGGGGTTTTATCCT
 421 S  D  I  A  V  E  W  E  S  N  G  Q  P  E  N  N  Y  K  T  T
1261 AGTGATATCGCCGTGGAATGGGAGTCAAACGGTCAGCCAGAGAACAATTACAAGACCACA
 441 P  P  M  L  D  S  D  G  S  F  F  L  Y  S  K  L  T  V  D  K
1321 CCCCCTATGCTGGACAGCGATGGGTCTTTCTTTCTGTATAGCAAACTGACAGTGGACAAG
 461 S  R  W  Q  Q  G  N  V  F  S  C  S  V  M  H  E  A  L  H  N
1381 TCTCGGTGGCAGCAGGGTAACGTCTTCTCTTGCAGTGTGATGCACGAAGCACTGCACAAT
 481 H  Y  T  Q  K  S  L  S  L  S  P  G  K  *
1441 CATTACACCCAGAAGTCACTGTCACTGAGCCCAGGAAAATGA
```

Figure 3

LONG-ACTING RECOMBINANT FOLLICLE-STIMULATING HORMONE AND USE THEREOF

TECHNICAL FIELD

The present disclosure relates to the fields of molecular biology and veterinary medication. More specifically, the present disclosure relates to a long-acting recombinant human follicle-stimulating hormone-Fc fusion protein, the preparation method and the use thereof. The fusion protein has significantly extended the half-life in vivo, and its therapeutic efficacy in the field of animal breeding is better than that of the existing follicle-stimulating hormone products.

BACKGROUND

Follicle-stimulating hormone (simply referred to as FSH) is a commonly used major drug ingredient in the field of animal breeding. The existing marketed FSH is mainly a biochemical species extracted from porcine pituitary and is applicable for early estrus and synchronous estrus of young sows, as well as for estrus stimulation of sows having delay in their estrus. It also has broader application in the field of the breeding of cattle and sheep. Biochemically extracted FSH has the defects such as virus contamination, limited sources of raw materials, collection difficulties, low content, and complex purification process. In addition, due to the limitations of the detection methods and the virus inactivation technology as well as the occurrence of unpredictable infection of new pathogenic virus, the possibility of the virus contamination of the biochemically extracted products cannot be completely eliminated.

In contrast, recombinant FSH has advantages that are unmatchable by biochemical FSH products in terms of purity, antigenicity, safety, and absence of viral infection. To date, no recombinant FSH product has been used in the field of veterinary medication. FSH is a glycosylated protein whose molecular weight is 43 KD as measured by SDS-PAGE. In addition, hFSH is a glycosylated protein comprising two single chains (an α chain and a β chain) connected by non-covalent bonds, and the correct folding of the two chains can ensure the bioactivity of hFSH. It remains a challenge to maintain the normal binding of the two chains during the expression and purification process of the protein. As a therapeutic drug, in order to ensure its biological activity, a necessary condition is to have the correct three-dimensional structure and glycosylation modification. Having perfect post-translational modification function is the main reason why mammalian cells are selected as the expression hosts of most biopharmaceutical proteins. Among all mammalian cells, Chinese Hamster Ovary Cell (CHO) is the most successful host cell for the expression of eukaryotic heterologous genes. More and more pharmaceutical recombinant proteins have achieved high-efficient expression in CHO cells, and many recombinant protein drugs for human use have already been marketed. Compared with other expression systems, this system has many advantages, such as having a complete post-translational processing process, including glycosylation and hydroxylation, so that the expression products of the heterologous eukaryotic genes can maintain their natural structure and activity, and the expression products are secreted extracellularly, which is favorable for the separation and purification of the exogenous proteins.

The amino acid sequence homology of FSH proteins between different mammalian species is very high. For example, the amino acid sequence homology of the α chain and β chain of human FSH to the α chain and β chain of porcine FSH are 83% and 96%, respectively, while the amino acid sequence homology of human FSH to bovine FSH is as high as 88%, suggesting the potential application of hFSH in the field of the breeding of other mammalian animals. Currently, pharmaceutical recombinant hFSH (human follicle-stimulating hormone, simply referred to as hFSH) produced by using CHO cells has been marketed. However, the following problems still exist. First, the expression amount of the recombinant hFSH produced by the existing methods is too low, its preparation process is complicated, and the production cost is too high. Secondly, the half-life thereof is short, requiring frequent administration by injection. Therefore, it is a challenge in this field to take advantage of molecular biology and cell culture method to develop hFSH drugs with biological activity and longer half-life.

SUMMARY

The present disclosure intends to provide a long-acting recombinant human follicle-stimulating hormone-Fc fusion protein (simply referred to as hFSH-Fc) and the preparation method and use thereof. The recombinant hFSH-Fc fusion protein is applied in the field of animal breeding and exhibits longer in vivo half-life and better efficacy as compared to the existing biochemically extracted products.

One object of the present disclosure is to provide a recombinant hFSH-Fc fusion protein. This fusion protein is a dimerized fusion protein and the amino acid sequence thereof successively comprises an hFSHβ subunit, CTP, an hFSHα subunit, a peptide linker (L for short) and human IgG2 Fc variant (vIgG2Fc) from N-terminal to C-terminal, as shown in SEQ ID NO: 2 (hFSHβ-CTP-hFSHα-L-vIgG2Fc amino acid sequence). The above fusion protein is abbreviated as hFSH-Fc.

The amino acid sequence of said hFSHβ subunit is one in which the amino acid residues 1-18 in the conventional hFSHβ subunit are deleted, as shown in SEQ ID NO: 5.

The amino acid sequence of said CTP (carboxy-terminal peptide) comes from the 28-34 amino acid residues of the carboxy-terminal of HCGβ chain, and preferably CTP is the 33 amino acid residues from the carboxy-terminal of HCGβ chain, as shown in SEQ ID NO: 4.

The sequence of the amino acid residues of said hFSHα subunit is one in which amino acid residues 1-24 in the conventional hFSHα subunit are deleted, as shown in SEQ ID NO: 3.

Said peptide linker contains 2-20 amino acid residues and the peptide linker contains two or more amino acid residues selected from glycine, serine, alanine and threonine. The amino acid sequence of the preferred peptide linker is GlySerGlyGlyGlySerGlyGlyGlyGlySerGlyGlyGlyGlySer, as shown in SEQ ID NO: 6.

Said human IgG2 Fc variant contains a human IgG2 hinge region with Pro331Ser mutation, a CH2 domain and a CH3 domain.

The function of human IgG Fc variant, peptide linker and CTP of the present disclosure are described hereinbelow in detail.

IgG Fc Variant

IgG class immunoglobulins are the most abundant proteins in human blood. Their half-life can reach as long as 21 days. An Fc fragment is the main reason for IgG to maintain long half-life in vivo, at the same time, it has a function in stabilizing proteins.

Fc comes from the Fc region of immunoglobulins, and Fc plays a significant role in immune defense for the elimination of pathogens. The effector function of IgG is mediated by Fc through two major mechanisms: (1) binding to the Fc receptors (FcγRs) on cell surface, leading to the digestion of pathogens via the antibody-dependent cellular cytotoxicity (ADCC) pathway, or (2) binding to the C1q part of the first complement component C1, initiating the complement-dependent cytotoxicity (CDC) pathway, thereby resulting in the lysis of pathogens. Among the four human IgG isotypes (IgG1, IgG2, IgG3, IgG4), human IgG2 hardly binds to FcγRs, and binds to C1q very weakly. For human therapeutic use, the Fc region of the recombinant fusion protein must not mediate adverse effector function, so that these cells may not be lysed or removed. Accordingly, the Fc region of hFSH-Fc must be non-lytic, that is, Fc is preferably inactive in terms of binding FcγRs and C1q thereby triggering the effector function. Obviously, none of the natural IgG isotypes is suitable for producing the recombinant dimerized hFSH-L-Fc protein. To obtain a non-lytic Fc, certain amino acids in the natural Fc region have to mutate to reduce the effector function thereof.

By analyzing the amino acid sequences of IgG isotypes, it is found that the Fc portion near the amino-terminal of the CH2 domain is shown to play a role in the binding of IgG Fc to FcγRs; and a portion which is critical in the binding to C1q is located near the carboxyl-terminal of the CH2 domain of human IgG. Human IgG2 does not bind to FcγRs but binds weakly to C1q. To minimize the effector function caused by the binding of Fc to C1q, the present disclosure uses human IgG2 Fc variant (vIgG2Fc) which contains a human IgG2 hinge region with Pro331Ser mutation, a CH2 domain and a CH3 domain (see FIG. 1). This Fc variant exhibits the minimized effector function as compared to the natural IgG2 Fc and is more suitable to prepare the recombinant hFSH-Fc fusion protein.

Peptide Linker

The length of the linker peptide plays an important role in the activity of the recombinant dimerized protein. Via long-term and in-depth studies, the inventors have designed a unique peptide linker of hinge region for the first time to reduce the steric hindrance effect, and can produce a recombinant dimerized protein in which the C-terminal of the hFSHα chain is coupled to the Fc variant via a flexible peptide linker. Instead of leading to the loss of the function of hFSH, this recombinant dimerized protein can maintain or even increase the bioactivity of the recombinant dimerized hFSH-Fc protein. The sequence of the amino acid residues of the preferable peptide linker is GlySerGlyGlyGlySerGlyGlyGlyGlySerGlyGlyGlyGlySer, as shown in SEQ ID NO: 6.

CTP

Glycosylation is very important to the activity and half-life of proteins. There are two types of glycosylation on proteins, N-linked glycosylation and O-linked glycosylation. CTP is a segment of 28-34 amino acid residues from the carboxy-terminal of HCGβ chain. It has been reported that HCG has a relatively longer half-life than hFSH, which is mainly due to this CTP peptide fragment. This CTP peptide fragment contains O-linked glycosylation sites; and can increase the glycosylation level of proteins, improve the activity of proteins and extend the in vivo half-life of proteins.

The recombinant hFSH-Fc fusion protein of the present disclosure has the following characteristics. This recombinant fusion protein is a dimerized fusion protein, and the amino acid sequence thereof successively comprises an hFSHβ subunit, CTP, an hFSHα subunit, a peptide linker and human IgG2 Fc variant from N-terminal to C-terminal. The human IgG2 Fc variant has the function of extending the in vivo half-life and stabilizing proteins. The Fc variant is non-lytic, and may reduce the effector function triggered by binding to FcγRs and C1q to the largest extent. CTP, which has no immunogenicity, may increase the protein activity and prolong the in vivo half-life. The α chain and the β chain of hFSH connected via CTP can lead to certain steric hindrance between the two chains, which is beneficial for the correct folding thereof without affecting functions. Coupling the C-terminal of the hFSH α chain to Fc variant via a flexible peptide linker can maintain or even increase the bioactivity of the recombinant hFSH-Fc fusion protein.

For the first time until the present disclosure, CTP, a peptide linker and human IgG2 Fc variant are linked in sequence into FSH to form a novel recombinant hFSH-Fc fusion protein, which is applied in the field of animal breeding for the first time. The alignment of the positions of human IgG2 Fc variant, CTP, and the peptide linker in this fusion protein can maintain the correct spatial configuration of FSH without affecting its bioactivity, and may prolong the half-life significantly. As compared with the existing dosage regimens for animal breeding, this fusion protein may significantly reduce the number of injections and has better efficacy.

Another object of the present disclosure is to provide a method for preparing the recombinant hFSH-Fc fusion protein. The preparation method comprises:

(1) constructing the gene expression vector encoding the recombinant hFSH-Fc fusion protein;

(2) stably expressing the recombinant hFSH-Fc fusion protein in mammalian host cells;

(3) culturing high-density cells for the production of the recombinant hFSH-Fc fusion protein;

(4) purifying and preparing the recombinant hFSH-Fc fusion protein.

Specifically, the steps of constructing the gene expression vector encoding the recombinant hFSH-Fc protein are as follows: using an artificial synthetic method to obtain a gene encoding the recombinant hFSH-Fc fusion protein, said gene is a codon-optimized nucleotide sequence (as shown in SEQ ID NO: 1); inserting the sequence into a mammalian cell expression vector (e.g., pCDNA3) or an improved expression vector (e.g., pCMV-DHFR), and obtaining the expression plasmid pCDNA3-hFSH-Fc containing hFSH-Fc target gene (FIG. 4). The optimization of the nucleotide sequence of the gene is selected and designed based on the preferred codons of the mammalian host cells.

Said mammalian cell expression vectors may be commercially available but not limited to vectors useful for the expression in eukaryotic cell systems, such as pCDNA3, pCMV/ZEO, pIRES, pDR, pBK, pSPORT, etc., preferably, pCDNA3.

The steps of stably expressing the recombinant hFSH-Fc fusion protein in mammalian host cells are as follows: transfecting the expression plasmid containing hFSH-Fc gene into suitable mammalian host cells; and screening and obtaining a cell strain with stable and high expression of the target protein.

Said mammalian host cells include CHO, HEK293, COS, BHK, NSO and Sp2/0 cells, preferably, CHO cells; and more preferably, dihydrofolate reductase (DHFR) deficient CHO cells that have been adapted to suspension culture in serum free medium (simply referred to as CHO DHFR−).

The transfection methods include calcium phosphate method, electroporation transfection method and liposome transfection, the preferred transfection method is electroporation transfection method.

The screening method is to first use a screening marker to perform screening; and then use an amplifiable selectable marker to select the cell strain which can improve the expression amount and obtain stable and high expression. The screening marker is any of the suitable selective resistance markers known in the art, for example, ZEO (Zeocin), G418 (aminoglycoside antibiotics), PUR (puromycin) or HYP (Hygromycin), the preferred resistance marker is ZEO. The screening marker may also be any of the fluorescent labeling genes known in the art, including GFP (Green Fluorescent Protein) and RFP (Red Fluorescent Protein), the preferred fluorescent labeling gene is GFP. The amplifiable selectable marker is DHFR sequence or GS (Glutaminesynthetase) sequence known in the art, the preferred amplifiable selectable marker is DHFR sequence. As the CHO-DHFR- cells themselves are lack of dihydrofolate reductase (DHFR), they cannot synthesize tetrahydrofolate on their own. Therefore, in order to survive, the addition of hypoxanthine, thymidine and glycine in the culture medium becomes essential. However, by the co-transfection of the target gene with the DHFR gene, not only cell clones that can grow in the culture medium free of the additives mentioned above, but also a MTX resistant cell line may be obtained. This is because DHFR can be inhibited by folic acid analogue MTX (methotrexate), and under the selective pressure of the concentration of MTX, DHFR gene must be amplified to a certain large copy number in order to survive. Further, as the target gene co-transfected with the DHFR gene is prone to integrate into the same domain of the cell chromosome together with the DHFR gene, the sequence fragment encoding the exogenous recombinant protein is amplified with the amplification of the DHFR gene, cell clones that express the exogenous protein in large amount may be obtained.

The steps of culturing the high-density cells for the production of the recombinant hFSH-Fc fusion protein are as follows. The above-mentioned stable cell stain obtained by screening is transferred to a shake flask or bioreactor to culture in large scale. Particularly, through the optimization of the cell culture condition, the present disclosure obtains a cell culture with high level expression of the recombinant hFSH-Fc fusion protein. The cell culture method of the present disclosure may accomplish the high-density cultivation of cells, increase the quality and yield of the recombinant protein, increase the extent of glycosylation of the recombinant protein, and enhance the content of sialic acid as well.

The optimization of said cell culture condition includes cooling culture method. Specifically, when the cell density reaches $1\times10^7$/mL, the temperature is reduced from 37° C. to 33° C. And then, the cells are cultured at 33° C. till the expression yield no longer increases. This method may increase the activity level of the expressed protein and the cumulative yield of the recombinant protein.

The optimization method of said cell culture condition also includes adding special additives in the culture medium, preferably, adding 100 LM $Cu^{2+}$ to the basal medium, and adding 2 mM ManNAc (N-acetyl-D-amino mannose) to the feeding medium. This method may increase the extent of glycosylation of the recombinant hFSH-Fc fusion protein, and improve the content of sialic acid by about 20%.

The steps of purification and preparation of the recombinant hFSH-Fc fusion protein are as follows:

1) Protein A affinity chromatography: performing centrifugation, collecting the supernatant, and performing chromatography using Protein A affinity column according to the characteristics of the protein-coupled Fc fragment of the present disclosure.

2) Purification by hydrophobic chromatographic column: according to the different hydrophobicity of the recombinant hFSH-Fc fusion protein, using hydrophobic chromatographic column to further remove the impurities in the target protein after the above Protein A purification.

Said hydrophobic chromatographic column includes Butyl Sepharose 4 Fast Flow, Octyl Sepharose 4 Fast Flow, Phenyl Sepharose 6 Fast Flow, Butyl-S Sepharose 6 Fast Flow, Butyl Sepharose 4B, Octyl Sepharose CL-4B, Phenyl Sepharose CL-4B, preferably, Phenyl Sepharose 6 Fast Flow.

The present disclosure discloses a preparation method of the recombinant hFSH-Fc fusion protein, and the recombinant hFSH-Fc fusion protein with high expression yield may be obtained by this preparation method. Due to its coupling to the IgG2 Fc variant, efficient and convenient purification may be achieved by the Protein A affinity chromatography. The purity of the fusion protein obtained after further purification via hydrophobic chromatography reaches 98% or more. In addition, the $\alpha$ chain and the $\beta$ chain of the recombinant hFSH-Fc fusion protein disclosed by the present disclosure may be correctly folded together, avoiding the formation of $\alpha$-$\alpha$ dimer and $\beta$-$\beta$ dimer, greatly simplifying the purification process and reducing the production cost.

Another object of the present disclosure is to provide a pharmaceutical composition comprising the long-acting recombinant hFSH-Fc fusion protein, wherein the pharmaceutical composition comprises a pharmaceutically acceptable carrier or excipient or diluent, and an effective amount of the long-acting recombinant hFSH-Fc fusion protein mentioned in the present disclosure.

Specifically, said pharmaceutical composition contains an effective amount (such as 0.000001-90 wt. %, preferably, 0.1-50 wt. %, more preferably, 5-40 wt. %) of the long-acting recombinant hFSH-Fc fusion protein of the present disclosure and a pharmaceutically acceptable carrier. Typically, an effective amount of the fusion protein of the present disclosure can be formulated in a non-toxic, inert and pharmaceutically acceptable aqueous carrier medium, wherein the pH is usually about 5-8, preferably, the pH is about 6-8.

Said pharmaceutical acceptable carrier includes (but is not limited to): sucrose, mannitol, Tween 20, methionine, saline, buffer, glucose, water, glycerol and compositions thereof. Typically, the pharmaceutical preparation should match with the mode of administration, the pharmaceutical composition of the present disclosure may be formulated into injection form, for example, prepared by conventional methods using physiological saline or aqueous solution containing glucose and other excipients. Said pharmaceutical composition is suitable to be manufactured under sterile condition. The dose of the active ingredient is the therapeutically effective amount. The pharmaceutical preparation of the present disclosure can also be formulated into a sustained release preparation.

The effective amount of the fusion protein mentioned in the present disclosure may vary according to the mode of administration and the severity of the disease to be treated. The selection of the preferred effective amount may be determined by those of ordinary skill in the art according to a variety of factors (such as by clinical trials). Said factors include but are not limited to the pharmacokinetic parameters of said fusion protein such as bioavailability, metabolism rate, half-life, and the like; and the severity of the disease of the animal to be treated, weight of the animal, immune status of the animal, administration route, etc.

A further object of the present disclosure is the application of the recombinant hFSH-Fc fusion protein in the field of animal breeding.

The in vivo half-life of the recombinant hFSH-Fc fusion protein of the present disclosure prolongs significantly, thus improving the pharmacokinetics and efficacy. As compared with the existing FSH, it may reduce the number of injections as well as the economic burden.

The advantages of the recombinant hFSH-Fc fusion protein of the present disclosure and its preparation method are summarized as follows.

1. The recombinant hFSH-Fc fusion protein of the present disclosure is a novel fusion protein formed by orderly coupling IgG2 Fc variant with CTP and hFSH. The recombinant hFSH-Fc fusion protein maintains the correct spatial configuration of FSH, and may significantly extend the in vivo half-life of the protein and greatly increase the expression amount of hFSH in CHO cells.

2. The α chain and the β chain of the dimerized single-chain hFSH-Fc fusion protein are folded correctly by covalent bonds, avoiding the formation of α-α dimer and β-β dimer, greatly simplifying the purification process and reducing the production cost.

3. The in vivo half-life of the recombinant hFSH-Fc fusion protein of the present disclosure is prolonged significantly. The half-life of the recombinant hFSH-Fc fusion protein is 10 times that of the existing porcine pituitary FSH, which may reduce the number of injections and has better therapeutic effect.

BRIEF DESCRIPTION OF THE DRAWINGS

FIG. 1 shows the comparison of the amino acid sequences of the hinge region of human IgG2 and its variants and CH2 domain. These three parts of the amino acid sequence are compared: amino acid domains 228, 234-237, and 330-331. The amino acid mutation of the variants is indicated in bold italics. The number of the amino acid residues is determined according to the EU numbering system.

FIG. 2 shows the schematic diagrams of the single-chain hFSH-Fc and the dimerized structure. a) single-chain hFSH-Fc; b) dimerized hFSH-Fc.

FIG. 3 shows the nucleotide sequence and the deduced amino acid sequence of hFSH-Fc of the HindIII-EcoRI fragment in the pCDNA3 expression vector. The nucleotide sequence of hFSH-Fc comprises the nucleotide sequence encoding leader peptide (1-18), hFSHβ chain, CTP, mature hFSHα chain, peptide linker, and IgG2Fc variant (vIgG2Fc). The mature recombinant hFSH-Fc fusion protein contains mature hFSHβ chain (19-129), CTP (130-162), mature α chain (163-254), peptide linker (255-270) and IgG2Fc variant (vIgG2Fc) (271-493).

DETAILED DESCRIPTION

The present disclosure will be further elaborated with specific examples hereinafter. It should be understood that these examples are merely used to illustrate the present disclosure and not to limit the scope of this disclosure. In the following examples, the experimental methods which specific conditions are not stated can be operated according to the conventional conditions such as the conditions mentioned in Sambrook et al., Molecular Cloning: A Laboratory Manual (New York: Cold Spring Harbor Laboratory Press, 1989), or the conditions recommended by the manufacturer.

Example 1: Construction of the Gene Expression Vector Encoding the Recombinant hFSH-Fc Fusion Protein The design of gene sequence was optimized on the basis of the preferred codons of CHO cells. The optimized fusion gene which contained gene encoding the signal peptide of the β chain of hFSH protein and its mature peptide fragment, CTP and the mature peptide fragment of hFSHα chain was synthesized by an artificial synthetic method. The synthesized DNA fragment of 756 bp in length was inserted into a transfer vector such as between the EcoRV restriction enzyme sites in pUC57 to give the hFSH plasmid (phFSH). The correctness of the inserted sequence was confirmed by DNA sequencing.

The fusion genes L-vIgG2Fc encoding a flexible peptide linker (Linker, detection "L") and an Fc variant (vIgG2Fc) fragment containing the restriction enzyme sites of BamHI (5'-end) and EcoRI (3'-end) were artificially synthesized respectively. The resulting fusion gene fragments were inserted into a transfer vector such as between the BamHI and EcoRI sites in PUC19 respectively to give a pL-vIgG2Fc plasmid which contained the gene encoding the Fc variant. The gene sequence of L-vIgG2Fc was confirmed by DNA sequencing. To prepare the hFSH-L-Fc fusion gene, the phFSH plasmid was double digested by the restriction enzymes SpeI and BamHI. The fusion gene fragments encoding the signal peptide of the β chain of hFSH protein and its mature peptide fragment, CTP and the mature peptide fragment of hFSH α chain were recycled after the gel electrophoresis. The purified above-mentioned gene fragments were then inserted to the 5'-end of the peptide linker in the pL-vIgG2Fc plasmid, linked by T4 ligase to construct a phFSH-L-vIgG2Fc plasmid. The constructed fusion gene comprised the gene encoding hFSHβ, CTP, hFSHα, peptide linker, and Fc variant. Its single-stranded structure was shown in FIG. 2a, the dimerized structure was shown in FIG. 2b.

Figure 4:
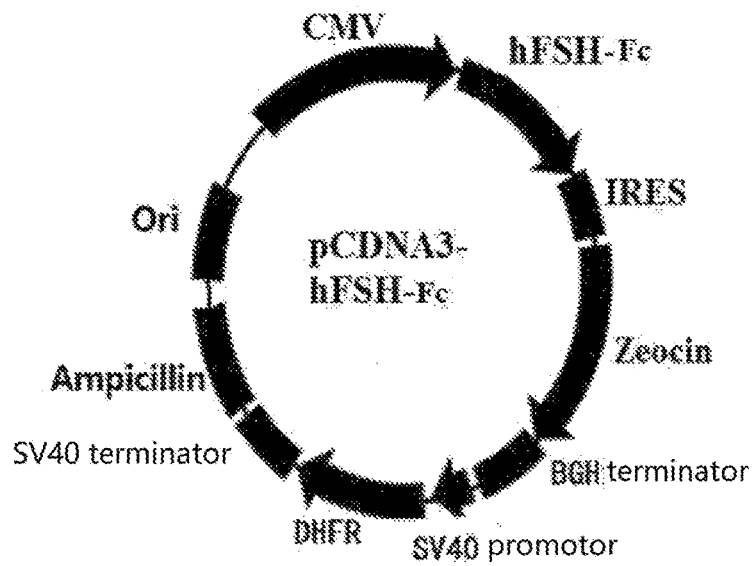
FIG. 4 shows a plasmid map of the constructed eukaryotic expression plasmid encoding the hFSH-Fc fusion protein. The full length of this expression plasmid is 9063 bp, comprising 10 major gene fragments, including: 1. CMV promoter, 2. target gene hFSH-Fc, 3. IRES, 4. Zeocin resistance screening gene, 5. BGH terminator, 6. SV40 promoter, 7. DHFR amplification gene, 8. SV40 terminator, 9. Ampicillin resistance gene (Ampicillin), 10. ColE1 replication origin (Ori).

The restriction enzymes SpeI/EcoRI were used to double digest the phFSH-L-vIgG2Fc plasmid, and the hFSH-L-vIgG2Fc fragment was obtained by DNA gel purification. The purified hFSH-L-Fc fragment was inserted between the corresponding restriction enzyme sites of the mammalian cell expression plasmid, such as pCDNA3 (Invitrogen), to finally obtain the expression plasmid pCDNA3-hFSH-L-vIgG2Fc (simply referred to as pCDNA3-hFSH-Fc plasmid) comprising the fusion gene, as shown in FIG. 4. This plasmid comprised the promoter CMV which was necessary for the mammalian cells to express the heterologous proteins with high efficiency; this plasmid also comprised two kinds of selective marker gene, leading to ampicillin resistance in bacteria and zeocin resistance in mammalian cells. In addition, when the host cells were deficient in DHFR gene expression, the dihydrofolate reductase (DHFR) gene of mice contained in PCDNA3 expression vector enabled the co-amplification of the pFSH-L-Fc fusion gene and the DHFR gene in the presence of methotrexate (MTX).

Connecting the α chain and the β chain of hFSH with the CTP peptide fragment was convenient for the right folding of the two chains. Coupling of hFSH and the Fc fragment by peptide linkers (preferably flexible linkers) might increase the bioactivity of the protein. For the present disclosure, a peptide linker of about 20 or fewer (but not less than 2) amino acids in length was preferred. As a matter of course, a peptide linker comprised of a single amino acid was within the protective scope of the present disclosure, it was preferred to use a peptide linker comprising or being comprised of two or more amino acids selected from the following amino acids: glycine, serine, alanine, and threonine. The peptide linker of an example of the present disclosure contained a Gly-Ser peptide member, and the amino acid sequence thereof was GlySerGlyGlyGlySerGlyGlyGlyGly-SerGlyGlyGlyGlySer, as shown in SEQ ID NO: 6.

Figure 6:
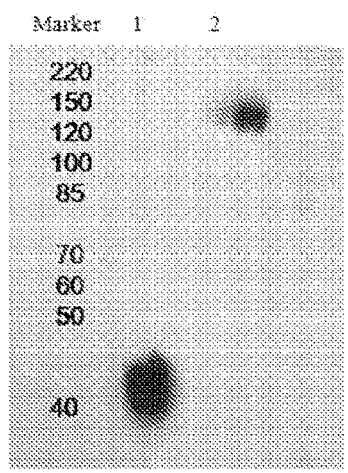
FIG. 6 shows successful expression of the recombinant hFSH-Fc fusion protein in CHO cells by the result of Western blotting analysis. Non-reduced gel, Lane 1: porcine pituitary FSH (about 43 kDa); Lane 2: the recombinant hFSH-Fc fusion protein of the present disclosure (about 140 kDa).

Example 2: Stable Expression of the Recombinant hFSH-Fc Fusion Protein in Mammalian Cells The expression plasmid pCDNA3-hFSH-L-Fc constructed in example 1 was transfected into DHFR-deficient CHO host cells (CHO-DHFR). FIG. 2b showed the schematic diagram of the recombinant dimerized hFSH-Fc fusion protein. The transfection was performed by electroporation method. A Gene Pulser Electroporator (Bio-Rad Laboratories, Hercules, Calif.) with a capacitance of 960 Fd was used and its electric field was set at 250V 10 μg of plasmid DNA linearized with PvuI was added to 2~5×10$^7$ cells in a cuvette. Two days following the transfection, the culture medium was changed to a growth medium containing 100 μg/mL of Zeocin resistance marker gene to obtain a transfectant that underwent the primary resistance screening. The expression of hFSH-Fc was examined by Western blotting method using anti-hFSH antibody, as shown in FIG. 6. DHFR amplifiable selectable marker gene was used to increase the expression level of the recombinant dimerized protein. For this purpose, the transfected recombinant dimerized protein gene was co-amplified using the DHFR gene in a growth medium containing increasing concentrations of MTX. Transfectants that could grow in a medium containing up to 10 μM/mL of MTX were subcloned using the limiting dilution method. The secretion rate of the subcloned cell lines was further analyzed. Cell strains with secretion level of more than about 10 (preferably about 20) g/10$^6$ (i.e., million) cells/24 hours were screened to obtain a cell line with stable and high expression of the recombinant hFSH-Fc fusion protein.

Figure 5:
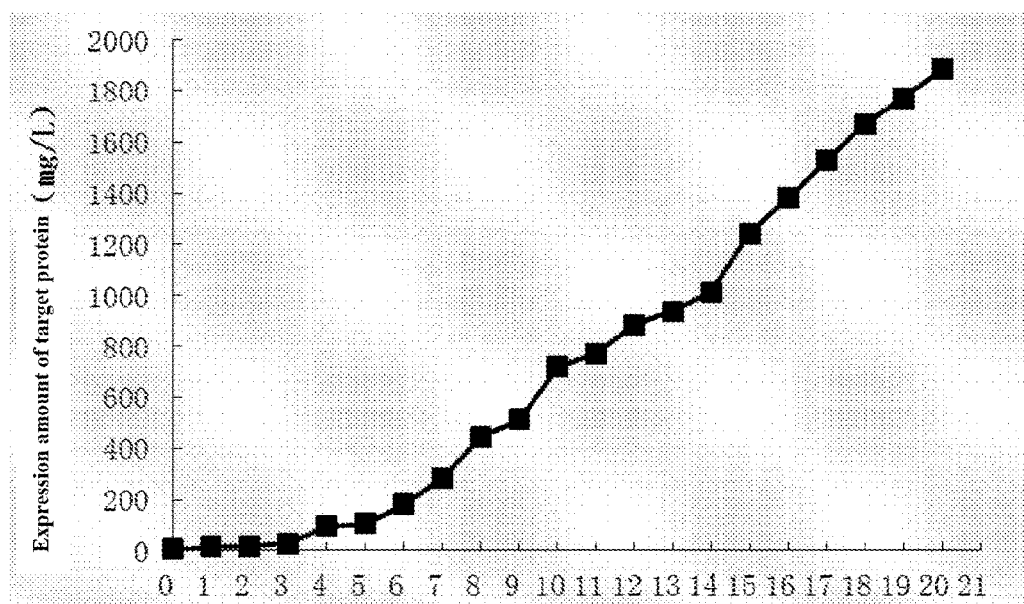
FIG. 5 shows the graph of the cumulative trend of the hFSH-Fc protein expressed and secreted by the recombinant hFSH-Fc cell strain in a 7 L bioreactor.

Example 3: Production and Purification of the Recombinant hFSH-Fc Fusion Protein The high-yield cell line obtained from Example 2 was first subjected to serum-free acclimation cultivation in a culture dish, and then transferred to a shake flask for suspension acclimation cultivation. During the acclimation process, medium screening was carried out at the same time. Different ingredients were added to observe the growth status and the growth trend of cells, as well as the biochemical indexes such as the activity of the expression products, sialic acid, etc. The following cell culture condition was preferred: basal medium comprising 100 μM $Cu^{2+}$, feeding medium comprising 2 mM ManNAc (N-acetyl-D-amino mannose). This method could increase the glycosylation extent of the recombinant hFSH-Fc fusion protein, and increase the content of sialic acid by about 20%. After successful acclimation, the cells were amplified to sufficient quantity. The cells were monitored and cultured in a 7 L bioreactor. When the cell density exceeded 1×10$^7$/mL, the culture temperature was reduced to 33° C., and the growth cycle for one batch was 20 days. The expression amount of the recombinant hFSH-Fc fusion protein was measured by affinity chromatography using a 1 ml Protein A column. The results showed that the cumulative yield expressed by the recombinant hFSH-L-vIgG2Fc cell line was 1.87 g/L (FIG. 5).

The purification of the recombinant hFSH-Fc fusion protein included the following steps:

1) Protein A affinity chromatography: performing centrifugation, collecting the supernatant, and according to the characteristics of the protein-coupled Fc fragment of the present disclosure, the supernatant was loaded onto a Protein A column equilibrated with phosphate buffer saline (PBS) by using affinity chromatography; after the binding of the recombinant fusion protein to Protein A, the column was washed with PBS until the OD 280 value was below 0.01. The bound recombinant FSH-Fc fusion protein was eluted with 20 mM sodium acetate buffer (pH 4.0), and lastly the active collected liquid was neutralized with 1 M Tris-HCl buffer (pH 10.0). The purity of the purified hFSH-Fc protein could reach 95% or more.

2) Hydrophobic column chromatography: the above-mentioned active collected liquid from the Protein A column was changed to 20 mM Tris-HCl-1.5 M NaCl (pH8.0) buffer by ultrafiltration method, and this sample was loaded onto a phenyl-6 Fast Flow column equilibrated with 20 mM Tris-HCl-1.5 M NaCl (pH8.0). The column was first washed with the same equilibration buffer, and then washed with 20 mM Tris-HCl-1.35 M NaCl (pH 8.0) before its elution with 20 mM Tris-HCl-0.5 M NaCl (pH 8.0) buffer.

Figure 7:
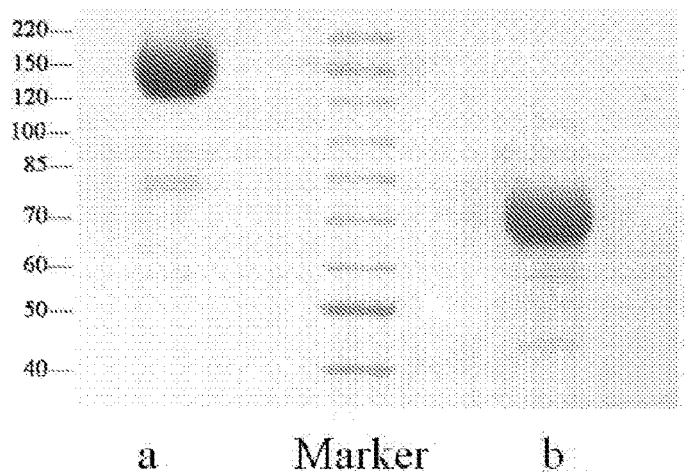
FIG. 7 shows a 10% SDS-PAGE electrophoretogram of the single-chain hFSH-Fc and the dimerized hFSH-Fc under reduced condition and non-reduced condition. a) reduced gel, single-chain hFSH-Fc (about 70 kDa); b) non-reduced gel, dimerized hFSH-Fc (about 140 kDa).

The result of Western blotting indicated the successful expression of the recombinant hFSH-Fc fusion protein in CHO cells. As shown in FIG. 6, in SDS-PAGE gel electrophoretogram under non-reduced condition, the porcine pituitary FSH (commercial product) and the recombinant hFSH-Fc fusion protein of the present disclosure showed the corresponding hybrid bands of the target protein at 43 kDa and 140 kDa respectively, confirming that the recombinant hFSH fusion protein obtained in the present disclosure contained FSH protein. FIG. 7 was the SDS-PAGE gel electrophoretogram of the purified hFSH-Fc fusion protein under reduced and non-reduced conditions. The result demonstrated that the purity of the purified hFSH-Fc protein could reach 98% or more. The molecular weight of the hFSH-Fc under reduced condition was half of that under non-reduced condition.

Example 4: In Vivo and In Vitro Activity Assay of the Recombinant hFSH-Fc Fusion Protein The in vitro activity (immunogenic activity) of the recombinant hFSH-Fc fusion protein of the present disclosure was assayed by the quantitative FSH enzyme immunoassay kit produced by BIOCHECK (USA) Company. Experimental method was conducted referring to the specification of the kit. The in vivo activity was assayed by the ovarian weight gain method in the 2010 edition of the British Pharmacopoeia. The measurement of the protein content was determined by LOWRY quantitative method. The HCG preparation was taken, and phosphate buffer (pH 7.2±0.2) solution containing 0.1% albumin was added to prepare a diluent of the test sample containing 70 IU/ml HCG Based on the labeled amount of the standard, the estimated potency of the porcine pituitary FSH and the recombinant hFSH-Fc fusion protein, the standard, the porcine pituitary FSH and the recombinant hFSH-Fc fusion protein were formulated with the diluent of the test sample (pH 7.2±0.2) into working solutions containing 3.33 IU/ml, 1.67 IU/ml and 0.83 IU/ml FSH (high, medium and low dose) respectively. Female Wistar rats of 19-28 days old were selected, however, the age difference should be no more than 3 days and the weight difference should be no more than 10 grams. The standard group, the porcine pituitary FSH group and the hFSH-Fc group were all divided into high-, medium- and low-dose group, and each group had 6 animals. The rats were injected subcutaneously into the back of the neck twice a day, 0.2 ml each time for 3 consecutive days, and the rats were dosed at the same time each day. 24 hours after the last injection, animals were killed in accordance with the sequence of administration by cervical dislocation. Ovaries were taken out and weighed after the surface moisture was blotted dry, and the weights of the organs were recorded. The activities of the porcine pituitary FSH and hFSH-Fc were calculated by the parallel line assay method based on quantitative response according to the ovarian weight gain of the standard group. The measured in vitro activities of the recombinant hFSH-Fc fusion protein and the porcine pituitary FSH were 10105 and 8321 IU/ml, respectively, and the in vivo activities thereof were 10230 and 7523 IU/ml, respectively. These results indicated that the recombinant hFSH-Fc fusion protein of the present disclosure had biological activity both in vitro and in vivo.

Example 5: Pharmacokinetic Assay of the Recombinant hFSH-Fc Fusion Protein

Figure 8:
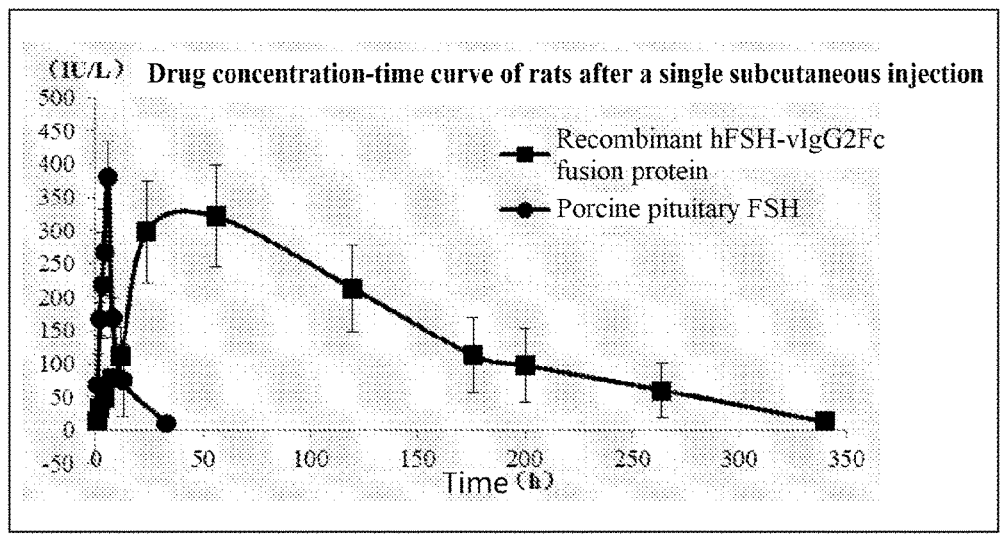
FIG. 8 shows the metabolic profiles of the purified recombinant hFSH-Fc fusion protein and the porcine pituitary FSH in rats.

The administration groups were divided into the recombinant hFSH-vIgG2Fc fusion protein of the present disclosure group and the porcine pituitary FSH group. In each group, five male Wistar rats weighing 200-250 grams per group were injected intramuscularly at 15 IU/kg respectively. Blood samples were collected at 1, 2, 3, 4, 6, 8, 12, 36 and 60 h after administration for the porcine pituitary FSH group and at 1, 2, 4, 8, 12, 24, 56, 120, 176, 200, 264 and 340 h after administration for the recombinant hFSH-Fc fusion protein group. The above samples were centrifuged at 3000 rpm for 5 min and the serum was taken and stored at −20° C. The immunological activity of FSH in plasma at each time point was tested by ELISA kit (BIOCHECK, USA). The main pharmacokinetic parameters of each group were calculated by statistical moment method using kinetica4.4 software. The pharmacokinetic curves of each group were shown in FIG. 8. The results of half-life were shown in Table 1. The results indicated that the elimination half-life of the porcine pituitary FSH in rats was about 3.05 h. However, the elimination half-life of the equal dose of the recombinant hFSH-vIgG2Fc fusion protein was approximately 47.24 h, which was 10 times or more of that of the porcine pituitary FSH.

TABLE 1

Half-life of the recombinant hFSH-Fc fusion protein and the porcine pituitary FSH

| Group | Half-life $T_{1/2}$ (h) |
| --- | --- |
| Recombinant hFSH-vIgG2Fc | 47.24 ± 13.92 |
| Porcine pituitary FSH | 3.05 ± 1.12 |

Example 6: Effect of the Recombinant hFSH-Fc Fusion Protein on Promoting the Early Estrus of Young Gilts Replacement gilts (6 months old, 90-100 kg) before puberty were selected and randomly divided into three groups: a recombinant hFSH-vIgG2Fc administration group (200 IU/head), a porcine pituitary FSH control group (200 IU/head), and a negative control group (physiological saline). In the above administration groups, 400 IU/head of HCG was used in combination, which might synergistically promote follicular maturation. The gilts were injected intramuscularly by group respectively, their estrus status were observed and recorded, and the estrus rate and synchronous estrus status were counted. The results were shown in Table 2. The data indicated that both the recombinant hFSH-Fc fusion protein and the porcine pituitary FSH could promote the early estrus of young gilts. However, the synchronous estrus rate within 3-4 days reached 80% or more in the recombinant hFSH-vIgG2Fc fusion protein group. The effect of the recombinant hFSH-vIgG2Fc fusion protein on promoting the early estrus of young gilts was better than that of the porcine pituitary FSH.

TABLE 2

Effect of the recombinant hFSH-Fc fusion protein on the early estrus of young gilts

| Group | Number of the tested gilts (head) | Estrus rate | Synchronous estrus rate within 3-4 days |
| --- | --- | --- | --- |
| Recombinant hFSH-vIgG2Fc | 30 | 93.3%**$^\Delta$ | 83.3%**$^\Delta$ |
| Porcine pituitary FSH | 30 | 53.3%* | 40%** |
| Negative control | 30 | 0 | 0 |

Note:
$\chi^2$ test, compared to the negative control group,
**p < 0.01,
*p < 0.05;
compared to the porcine pituitary FSH control group, $^\Delta$p < 0.05.

Example 7: Therapeutic Effect of the Recombinant hFSH-Fc Fusion Protein on Replacement Sows in Anestrus Replacement sows in anestrus older than 10 months and weighing 140 kg or more were selected and injected with 1 ml of cloprostenol injection to eliminate the non-estrus cases caused by the generation of permanent corpus luteum, and were then randomly divided into three groups: a recombinant hFSH-vIgG2Fc fusion protein administration group (200 IU/head), a porcine pituitary FSH control group (200 IU/head), and a negative control group (physiological saline). In the above administration groups, 400 IU/head of HCG was used in combination, which might synergistically promote follicular maturation. The sows were intramuscularly injected by group respectively, and their estrus and conception status were observed and recorded. The results were shown in Table 3. The data indicated that the recombinant hFSH-vIgG2Fc fusion protein could significantly increase the estrus rate of the replacement sows in anestrus, and showed significant difference (P<0.01) relative to the negative control group. The recombinant hFSH-vIgG2Fc fusion protein group also achieved higher results as compared to the porcine pituitary FSH control group (P<0.05). In addition, the recombinant hFSH-vIgG2Fc fusion protein group also had a conception rate in estrus that was significantly higher than that of the negative control group and the porcine pituitary FSH control group. Besides, the difference among the above groups was statistically significant (P<0.05).

TABLE 3

Therapeutic effect of the recombinant hFSH-Fc fusion protein on replacement sows in anestrus

| Group | Number of the tested sows | Estrus rate | Conception rate in estrus |
|---|---|---|---|
| Recombinant hFSH-vIgG2Fc | 60 | 40%**Δ | 75%*Δ |
| Porcine pituitary FSH | 60 | 28.3%* | 47.1% |
| Negative control | 60 | 6.7% | 25% |

Note:
$\chi^2$ test, compared to the negative control group,
**p < 0.01,
*p < 0.05;
compared to the porcine pituitary FSH group, $^\Delta$p < 0.05.

Example 8: Therapeutic Effect of the Recombinant hFSH-Fc Fusion Protein on Delayed Estrus of Multiparous Sows Multiparous sows that did not enter estrous two weeks after weaning were selected and injected with 1 ml of cloprostenol injection to eliminate the non-estrus cases caused by the generation of permanent corpus luteum, and were then randomly divided into three groups: a recombinant hFSH-vIgG2Fc fusion protein administration group (200 IU/head), a porcine pituitary FSH control group (200 IU/head) and a negative control group (physiological saline). In the above administration groups, 400 IU/head of HCG was used in combination, which might synergistically promote follicular maturation. The sows were intramuscularly injected by group, and their estrus and conception status were observed and recorded. The results were shown in Table 4. The data indicated that both the recombinant hFSH-Fc fusion protein and the porcine pituitary FSH could increase the estrus rate of the multiparous sows which did not enter estrus 2 weeks after weaning. However, as compared to the negative control group and the porcine pituitary FSH group, the recombinant hFSH-vIgG2Fc fusion protein group had better therapeutic effect and had significant difference relative to the negative control group (P<0.01). The recombinant hFSH-vIgG2Fc fusion protein group also had higher conception rate in estrus than that of the porcine pituitary FSH control group and the negative control group. The difference among the above groups was statistically significant (P<0.05).

TABLE 4

Therapeutic effect of the recombinant hFSH-Fc fusion protein on delayed estrus of multiparous sows

| Group | Number of the tested sows | Estrus rate | Conception rate in estrus |
|---|---|---|---|
| Recombinant hFSH-vIgG2Fc | 38 | 63.1%**Δ | 87%*Δ |
| Porcine pituitary FSH | 37 | 27.3%* | 60% |
| Negative control | 38 | 7.9% | 33.3% |

Note:
$\chi^2$ test, compared to the negative control group,
**p < 0.01,
*p < 0.05;
compared to the porcine pituitary FSH group, $^\Delta$p < 0.05.

Example 9: Synchronous Estrus Effect of the Recombinant hFSH-Fc Fusion Protein on Dairy Goats in the Central Shaanxi Plain During the Breeding Season During the breeding season (from September to November) of dairy goats in the central Shaanxi plain, healthy ewes aged 1 to 3 years old and weighing 50 to 75 kg, with moderate or better body condition and no reproductive disease, were selected to conduct the test. The test was conducted in three groups: a recombinant hFSH-vIgG2Fc administration group, a pituitary FSH control group, and a blank negative control group. Each group of ewes was treated with progesterone vaginal suppository sponge (CIDR) for 12 days. In the recombinant hFSH-vIgG2Fc group, 40 units of the corresponding drug were intramuscularly injected 24 hours before the removal of the suppository. The ewes of the pituitary FSH control group were intramuscularly injected with 25 units of pituitary FSH at 24 h and 12 h before the removal of the suppository, respectively. The ewes of the blank negative control group were intramuscularly injected with the same volume of physiological saline at 24 h and 12 h before the removal of the suppository. All three groups were injected with 0.1 mg cloprostenol at the removal of the suppository. From 12 h after the removal of the suppository, rams were used every 12 hours to test the estrus. It was deemed as estrus when the ewes approached the rams, fluttered tails, allowed the mounting of rams or ewes. The synchronous estrus treatment was deemed effective for ewes entering estrus within 96 h, and the estrus rate was calculated. 5 days after the completion of estrus, ovulation and the development of corpus luteum in ovaries of the ewes in estrus were observed with laparoscope. The number of the ewes with normally developed ovarian follicle, ovulation and the formation of normally functioned corpus luteum in ovary were recorded, and the rate of ovulating and forming functional corpus luteum was calculated.

The results (Table 5) indicated that, as compared to the negative control group, both the recombinant hFSH-vIgG2Fc and the pituitary FSH could significantly increase the estrus rate (P<0.01), which meant that both drugs had significant effect on promoting the estrus of goats. However, the recombinant hFSH-Fc fusion protein of the present disclosure demanded smaller dose and fewer administrations as compared to the pituitary FSH.

TABLE 5

Synchronous estrus effect of the recombinant hFSH-Fc fusion protein on dairy goats in central Shaanxi plain during the breeding season within 96 h after the removal of the suppository

| Group | Number of the dairy goats under treatment | Estrus rate | Rate of ovulating and forming functional *corpus luteum* |
|---|---|---|---|
| Blank negative control group | 45 | 22% | 20% |
| Pituitary FSH control group | 45 | 91.1%* | 68.3%* |
| Recombinant hFSH-vIgG2Fc administration group | 45 | 93.3%* | 71.4%* |

$\chi^2$ test: compared to the blank negative control group,
*$P < 0.01$.

What is claimed is:

1. A method for animal breeding in a subject thereof, comprising administering a recombinant homodimeric hFSH-Fc fusion protein to the subject, wherein the recombinant homodimeric hFSH-Fc fusion protein with an amino acid sequence sequentially comprising an hFSH β-subunit, CTP, hFSH α-subunit, a flexible peptide linker, and human IgG2 Fc variant, from N-terminal to C-terminal, wherein said human IgG2 Fc variant comprises a hinge with a Pro331Ser mutation, CH2, and CH3 domains; and wherein the amino acid sequence of the fusion protein is set forth in SEQ ID NO:2.

* * * * *

SEQUENCE LISTING

<160> NUMBER OF SEQ ID NOS: 5

<210> SEQ ID NO 1
<211> LENGTH: 1482
<212> TYPE: DNA
<213> ORGANISM: Human

<400> SEQUENCE: 1

```
atgaagaccc tgcagttctt tttcctgttt tgctgttgga aggcaatctg ctgtaactca      60
tgtgagctga ctaatatcac cattgccatc gaaaaagagg aatgcaggtt ctgtattagt     120
atcaacacta cctggtgcgc tggctactgt tatacaaggg atctggtgta taggaccca     180
gcacggccca aaatccagaa gacatgcact ttcaaagaac tggtgtacga gactgtgagg     240
gtccctggct gtgcccacca tgctgattcc ctgtacactt atccagtggc cacccagtgc     300
cactgtggaa agtgcgatag tgactcaaca gactgtactg tgcgaggcct gggaccttct     360
tactgcagtt ttggcgaaat gaaggagccc cgtttccagg attccagctc tagtaaagct     420
cccctcctt ccctgccctc accctcaaga ctgcctggac cttccgacac tcccatcctg     480
ccacaggccc ccgatgtgca ggactgccct gaatgtactc tgcaggagaa ccccttcttt     540
tctcagcccg cgctcctat cctgcagtgt atgggatgct gttttagtag agcatatcct     600
accccactgc gctcaaagaa aacaatgctg gtccagaaga atgtgacaag cgaatctact     660
tgctgtgtgg ctaaatccta caaccgcgtg accgtgatgg gcggcttcaa ggtggagaat     720
cacacagcat gccattgttc tacttgctac taccataaga gtggatccgg tggcggttcc     780
ggtggaggcg gaagcggcgg tggaggatca gtggagtgcc ctccatgtcc agcaccccct     840
gtcgcaggtc catctgtgtt cctgtttcca cccaagccta agacactct gatgatctcc     900
cgcacccag aagtcacctg tgtggtcgtg gatgtgagcc atgaagaccc cgaggtccag     960
ttcaattggt acgtggatgg cgtcgaggtg cacaacgcta agacaaaacc tagagaagag    1020
cagttcaact ctaccttcg cgtcgtgagt gtgctgacag tcgtgcacca ggactggctg    1080
aatgcaagg agtataagtg caaagtgagc aacaaaggac tgcctgcctc aatcgaaaag    1140
actatttcca agaccaaagg acagccaaga gagcccagg tgtacaccct gcctccaagc    1200
cgcgaagaga tgactaaaaa tcaggtctct ctgacctgtc tggtgaaggg tttatcct    1260
agtgatatcg ccgtggaatg ggagtcaaac ggtcagccag agaacaatta caagaccaca    1320
cccccctgc tggacagcga tggtctttc tttctgtata gcaaactgac agtggacaag    1380
tctcggtggc agcagggtaa cgtcttctct tgcagtgtga tgcacgaagc actgcacaat    1440
cattacaccc agaagtcact gtcactgagc ccaggaaaat ga                       1482
```

-continued

```
<210> SEQ ID NO 2
<211> LENGTH: 493
<212> TYPE: PRT
<213> ORGANISM: Human

<400> SEQUENCE: 2

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu Pro Arg Phe Gln Asp Ser Ser Ser Lys Ala Pro Pro Pro Ser
130                 135                 140

Leu Pro Ser Pro Ser Arg Leu Pro Gly Pro Ser Asp Thr Pro Ile Leu
145                 150                 155                 160

Pro Gln Ala Pro Asp Val Gln Asp Cys Pro Glu Cys Thr Leu Gln Glu
                165                 170                 175

Asn Pro Phe Phe Ser Gln Pro Gly Ala Pro Ile Leu Gln Cys Met Gly
            180                 185                 190

Cys Cys Phe Ser Arg Ala Tyr Pro Thr Pro Leu Arg Ser Lys Lys Thr
        195                 200                 205

Met Leu Val Gln Lys Asn Val Thr Ser Glu Ser Thr Cys Cys Val Ala
210                 215                 220

Lys Ser Tyr Asn Arg Val Thr Val Met Gly Gly Phe Lys Val Glu Asn
225                 230                 235                 240

His Thr Ala Cys His Cys Ser Thr Cys Tyr Tyr His Lys Ser Gly Ser
                245                 250                 255

Gly Gly Gly Ser Gly Gly Gly Ser Gly Gly Gly Ser Val Glu
            260                 265                 270

Cys Pro Pro Cys Pro Ala Pro Pro Val Ala Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser His Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Phe Arg Val Val Ser Val Leu
            340                 345                 350

Thr Val Val His Gln Asp Trp Leu Asn Gly Lys Glu Tyr Lys Cys Lys
        355                 360                 365

Val Ser Asn Lys Gly Leu Pro Ala Ser Ile Glu Lys Thr Ile Ser Lys
370                 375                 380
```

-continued

Thr Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
        420                 425                 430

Pro Glu Asn Asn Tyr Lys Thr Thr Pro Pro Met Leu Asp Ser Asp Gly
    435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 3
<211> LENGTH: 92
<212> TYPE: PRT
<213> ORGANISM: Human

<400> SEQUENCE: 3

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 4
<211> LENGTH: 33
<212> TYPE: PRT
<213> ORGANISM: Human

<400> SEQUENCE: 4

Pro Arg Phe Gln Asp Ser Ser Ser Ser Lys Ala Pro Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 5
<211> LENGTH: 111
<212> TYPE: PRT
<213> ORGANISM: Human

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

-continued

```
Lys Thr Cys Thr Phe Lys Glu Leu Val Tyr Glu Thr Val Arg Val Pro
    50                  55                  60
Gly Cys Ala His His Ala Asp Ser Leu Tyr Thr Tyr Pro Val Ala Thr
65                  70                  75                  80
Gln Cys His Cys Gly Lys Cys Asp Ser Asp Ser Thr Asp Cys Thr Val
                85                  90                  95
Arg Gly Leu Gly Pro Ser Tyr Cys Ser Phe Gly Glu Met Lys Glu
            100                 105                 110
```